United States Patent [19]

Honda et al.

[11] Patent Number: 5,220,049
[45] Date of Patent: Jun. 15, 1993

[54] METHOD FOR PREPARING UNSATURATED COMPOUNDS

[75] Inventors: Tadatoshi Honda; Kazuhiro Terada, both of Kanagawa, Japan

[73] Assignee: Mitsui Toatsu Chemicals, Inc., Tokyo, Japan

[21] Appl. No.: 977,778

[22] Filed: Nov. 17, 1992

Related U.S. Application Data

[62] Division of Ser. No. 610,945, Nov. 9, 1990.

[30] Foreign Application Priority Data

| Nov. 15, 1989 | [JP] | Japan | 1-295101 |
| Nov. 30, 1989 | [JP] | Japan | 1-309098 |
| Nov. 30, 1989 | [JP] | Japan | 1-309099 |

[51] Int. Cl.$^5$ .......................................... C07C 253/24
[52] U.S. Cl. ................................................. 558/319
[58] Field of Search ........................................ 558/319

[56] References Cited

U.S. PATENT DOCUMENTS

| 3,161,670 | 12/1964 | Adams et al. | 558/319 X |
| 3,321,507 | 5/1967 | Ginnasi | 558/319 |
| 3,365,482 | 1/1968 | Khoobiar | 558/319 |
| 3,678,090 | 7/1972 | Taylor | 558/319 |
| 4,368,346 | 1/1983 | Eastman | 585/658 |
| 4,751,342 | 6/1988 | Kimble | 585/623 |
| 4,788,317 | 11/1988 | Guttmann et al. | 558/319 |
| 4,837,233 | 6/1989 | Glaeser et al. | 558/319 X |
| 4,866,195 | 9/1989 | Brazdil, Jr. et al. | 558/319 |
| 4,871,706 | 10/1989 | Brazdil, Jr. et al. | 558/319 X |
| 4,883,895 | 11/1989 | Brazdil, Jr. et al. | 558/319 |
| 4,888,438 | 12/1989 | Glaeser et al. | 558/319 |
| 4,918,214 | 4/1990 | Brazdil, Jr. et al. | 558/319 |

FOREIGN PATENT DOCUMENTS

| 189282 | 7/1986 | European Pat. Off. . |
| 337028 | 10/1989 | European Pat. Off. . |

*Primary Examiner*—Joseph Paul Brust
*Attorney, Agent, or Firm*—Burns, Doane, Swecker & Mathis

[57] ABSTRACT

A method for preparing an unsaturated compound mainly comprising monoolefins, or a mixture of $\alpha, \beta$-unsaturated nitriles and monoolefins comprises coming a mixed gas which comprises paraffins and oxygen, or paraffins, oxygen and ammonia in contact with a catalyst which comprises (1) an oxide of phosphorus and (2) at least one oxide selected from the group consisting of indium oxide and tin oxide or comprises, in addition to the foregoing catalytic components, (3) at least one oxide selected from the group consisting of vanadium oxide, tungsten oxide and molybdenum oxide. The method makes it possible to prepare monoolefins, or a mixture of $\alpha, \beta$-unsaturated nitriles and monoolefins in high yield and high selectivity from cheap starting materials, parafins.

12 Claims, No Drawings

METHOD FOR PREPARING UNSATURATED COMPOUNDS

This application is a divisional of application Ser. No. 07/610,945, filed Nov. 9, 1990.

BACKGROUND OF THE INVENTION

(1) Field of the Invention

The present invention relates to a method for preparing unsaturated compounds from paraffinic compounds and more specifically to a method for preparing unsaturated compounds mainly comprising monoolefins by an oxidative dehydrogenation of paraffins in the presence of a specific catalyst or a method for preparing unsaturated compounds mainly comprising α, β-unsaturated nitriles and monoolefins by ammoxidation of paraffins in the presence of a specific catalyst.

(2) Description of the Prior Art

There has been known an oxidative dehydrogenation reaction of hydrocarbons as a method for preparing unsaturated compounds having a carbon-carbon double bond and there have been known two approaches to such an oxidative dehydrogenation reaction of hydrocarbons. The first approach comprises oxidatively dehydrogenating monoolefins to give diolefins. For instance, U.S. Pat. No. 3,274,283 discloses a method for preparing butadienes by oxidative dehydrogenation of butenes in the presence of a catalyst obtained by impregnating tin oxide with phosphoric acid to thus form phosphoric acid-supporting tin oxide. Subsequently, there have been proposed some methods for preparing diolefins in which a catalyst comprising an oxide of tin and phosphorus.

The second approach comprises oxidatively dehydrogenating paraffins to give olefins. For instance, U.S. Pat. Nos. 3,502,739; 3,801,671 and 3,927,138 disclose methods in which Group VIII metals are used as catalysts for preparing diolefins. In addition, a method for preparing monoolefins is disclosed in E.P. No. 0,189,282 (1986). The European Patent comprises oxidatively dehydrogenating ethane, propane or isobutane in the presence of a catalyst comprising an oxide of tin and phosphorus to form ethylene, propylene or isobutene respectively, the oxidative dehydrogenation being performed at a reaction temperature ranging from 200° to 700° C. and a reaction pressure ranging from 1 to 50 bar. However, only the embodiment of the preparation Of ethylene from ethane is clearly disclosed in Examples of the specification of the European Patent and the reaction temperature of 550° C. is simply disclosed. High selectivity is achieved only when the reaction is performed at a high pressure. It is commonly believed that a complete oxidation reaction is predominant if the reaction is performed at ordinary pressure as described in J. Chem. Soc., Chem. Commun., 1986, p. 1058.

J. Catal., 1978, 52, p. 116 discloses an oxidative dehydrogenation reaction of ethane with an Mo-V catalyst and reports that the ethylene selectivity is 100% at an ethane conversion of 10% and the ethylene selectivity is 83% at an ethane conversion of 25%. Moreover, it reports that if propane is used as a starting material, the products comprise only acetic acid, acetaldehyde, CO and $CO_2$ and any propylene is not produced.

As has been described above, setting aside the preparation of ethylene, there has not yet been proposed any catalytic system having high selectivity in the production of an olefin such as propylene or isobutene through an Oxidative dehydrogenation reaction of an olefin.

Recently, Japanese Patent Unexamined Publication (hereinafter referred to as "J.P. KOKAI") No. Sho 63-295546 which relates to an ammoxidation reaction of propane discloses an example in which a V-Sb-W/Al system as a catalyst is used and the patent reports that the propylene selectivity of 52.8% was attained at a propane conversion of 18.3%. However, the selectivity is still unsatisfied.

In addition, many attempts have been directed to the production of acrylonitrile by ammoxidation of propane noticing the difference in price between propane and propylene. However, a high reaction temperature in the order of 500° C. is required in these methods and the addition of a halogen or sulfur compound is also required for improving the activity and selectivity of catalysts used, which in turn requires the use of devices and materials of high quality. As has been explained above, there has not yet been proposed any industrially acceptable method for preparing acrylonitrile from propane as a starting material irrespective of the difference in price between propane and propylene. The same may be said of the ammoxidation of butanes.

SUMMARY OF THE INVENTION

Accordingly, a first object of the present invention is to provide a method for preparing unsaturated compounds mainly comprising monoolefins in high selectivity through oxidative dehydrogenation of paraffins carried out in the presence of a catalyst having a specific composition.

A second object of the present invention is t provide a method capable of producing unsaturated compounds mainly comprising α, β-unsaturated nitriles and monoolefins through ammoxidation of paraffins performed in the presence of a catalyst having a specific composition.

The inventors of this invention have conducted various studies to achieve the foregoing objects and have completed the present invention.

According to an aspect of the present invention, there is provided a method for preparing an unsaturated compound mainly comprising monoolefins wherein a mixed gas containing paraffins and oxygen is brought into contact with a catalyst which comprises (1) an oxide of phosphorus and (2) an oxide of indium.

According to a second aspect of the present invention, there is provided a method for preparing an unsaturated compound mainly comprising monoolefins wherein a mixed gas containing paraffins, oxygen and ammonia is brought into contact with a catalyst which comprises (1) an oxide of phosphorus and (2) at least one oxide selected from the group consisting of indium oxide and tin oxide.

According to a third aspect of the present invention, there is provided a method for preparing an unsaturated compound mainly comprising α, β-unsaturated nitriles and monoolefins wherein a mixed gas containing paraffins having at least 3 carbon atoms, oxygen and ammonia is brought into contact with a catalyst which comprises (1) an oxide of phosphorus, (2) at least one oxide selected from the group consisting of indium oxide and tin oxide and (3) at least one oxide selected from the group consisting of vanadium oxide, tungsten oxide and molybdenum oxide.

DESCRIPTION OF THE PREFERRED EMBODIMENTS

The catalyst used in the method of the present invention comprises (1) an oxide of phosphorus and (2) at least one member selected from the group consisting of indium oxide and tin oxide; or (1) an oxide of phosphorus, (2) at least One oxide selected from the group consisting of indium oxide and tin oxide and (3) at least one oxide selected from the group consisting of vanadium oxide, tungsten oxide and molybdenum oxide.

The foregoing catalysts can be prepared according to the methods commonly used in this art. For instance, a compound oxide of phosphorus and tin or indium is prepared according to any one of the following methods:

① a method comprising mixing a tin oxide or indium oxide and a phosphorus oxide (in general, phosphoric acid is employed);

② a method comprising stepwise hydrolyzing or simultaneously hydrolyzing an easily hydrolyzable compound of tin or indium and an easily hydrolyzable phosphorus compound; or ③ a method comprising mixing an easily hydrolyzable compound or a hydrolyzate of tin or indium and a phosphorus oxide (in general, phosphoric acid is employed), and the resulting compound oxide per se is used as a catalyst; or the compound oxide is further treated according to the following method:

(a) a method comprising mixing the compound oxide with an easily hydrolyzable compound or a hydrolyzate of at least one element selected from the group consisting of vanadium, tungsten and molybdenum; or a compound oxide of at least one element selected from the group consisting of vanadium, tungsten and molybdenum and phosphorus and then calcining the resulting mixture; or (b) a method comprising preparing a compound oxide of a tin or indium oxide with an oxide of at least one element selected from the group consisting of vanadium, tungsten and molybdenum, mixing the resulting compound oxide with an easily hydrolyzable compound or oxide of phosphorus (in general, phosphoric acid is employed) and then calcining the mixture.

The ratio of tin or indium to phosphorus is not critical in the present invention, but in general it ranges from 0.05 to 4 expressed in the atomic ratio, P/Sn or P/In or P/(Sn+In).

The contents of vanadium, tungsten and molybdenum are not critical in the invention.

The catalysts used in the method of this invention may further comprises, in addition to tin, indium, phosphorus, vanadium, tungsten and molybdenum, other elements for improving the activity and selectivity of the catalyst. Examples of such elements are Li, Na, K, Rb, Cs, Mg, Ca, Sr, Ba, Y, La, Ti, Zr, Nb, Ta, Zn, Cd, B, Al, Ga, Si, Ge, Pb, As, Sb, Bi, Se and Te.

Moreover, the catalyst can be used in the state supported by a carrier such as silica, alumina, silicon carbide, aluminum nitride, titania or zirconia as has been commonly adopted in this art.

The paraffins used as starting materials in the method of the present invention are not restricted to specific ones, but preferred examples thereof are ethane, propane and butanes, in particular propane and isobutane because they can easily be available and usefulness of the resulting olefins and nitriles.

The sources Of oxygen gas for preparing a mixed gas used in the method of this invention are not also restricted to specific ones, but in general pure oxygen, air or the like may be used. The molar ratio of paraffins to oxygen in the mixed gas is not critical, but is selected so that combustion is not caused in view of safety and in general ranges from 1:0.1~1.0.

Moreover, the starting gas mixture may be diluted with an inert gas such as herium, argon, nitrogen, carbon dioxide and water vapor.

If the mixed gas used in the method contains ammonia, it may be supplied as a dry gas or may be supplied by evaporating aqueous ammonia with an evaporator.

In this case, the molar ratio: paraffins/oxygen/ammonia is not restricted to a specific value, but is selected so that combustion is not caused in view of safety and in general ranges from 1:0.1~1.0:0.05~0.5.

The reaction temperature varies depending on various factors such as the kinds of starting materials used, concentration of the starting material, molar ratio of the mixed gas and contact time and in general it ranges from 200° to 700° C., preferably 200° to 500° C.

The reaction pressure in general ranges from 1 to 50 bar and preferably 1 to 3 bar.

As has been described above in detail, according to the method of the present invention, monoolefins or a mixture of $\alpha, \beta$-unsaturated nitriles and monoolefins can be prepared in high yield and high selectivity from the corresponding paraffins as starting materials which are cheaper than olefins conventionally used as starting materials.

The method of the present invention will hereunder be explained in more detail with reference to the following non-limitative working Examples. Moreover, the practical effects attained by the present invention will also be discussed in detail in comparison with Comparative Examples.

EXAMPLE 1

354.9 g of indium nitrate (available from Mitsuwa Chemical and Pharmaceutical Co., Ltd.) was added to and dissolved in 3,000 ml of water heated to 40° C. and then a solution of 203.1 g of triammonium phosphate (available from Kanto Chemical Co., Ltd.) in 1,000 ml of water was added to the resulting solution to thus form precipitates. The precipitates were decanted and then filtered under suction. The resulting filter cake was dried at 120° C. for 5 hours and further calcined at 500° C. for 4 hours. The calcined filter cake was pulverized into fine particles of 10 to 32 mesh and was used as a catalyst.

8 cc of the catalyst was packed in a reactor of stainless steel (SUS 316) having an inner diameter of 17 mm. A mixed gas comprising propane/oxygen/ammonia having a molar ratio of 10/6/3 was supplied at a space velocity (SV) of 1000 hr$^{-1}$ while the temperature of the reactor was maintained at 460° C. After 15 hours, the reaction gas was analyzed and it was found that the conversion of propane was 8%, that of oxygen was 22% and the selectivity of propylene was 65%.

EXAMPLE 2

The same procedures used in Example 1 were repeated except that isobutane was substituted for propane and that the reaction was performed at 430° C. As a result, it was found that the conversion of isobutane was 7% and that the selectivity of isobutene was 52%.

EXAMPLE 3

The same procedures used in Example 1 were repeated except that ammonia was not used. As a result, it was found that the conversion of propane was 15% and that the selectivity of propylene was 45%.

EXAMPLE 4

The same procedures used in Example 3 were repeated except that isobutane was substituted for propane and that the reaction was performed at 430° C. As a result, it was found that the conversion of isobutane was 14% and that the selectivity of isobutene was 32%.

EXAMPLE 5

225.6 g of stannous chloride (available from Kanto Chemical Co., Ltd.) was added to and dissolved in 1,000 ml of a 0.5N HCl solution heated to 40° C. and then a solution of 135.3 g of triammonium phosphate (available from Kanto Chemical Co., Ltd.) in 1,000 ml of water was added to the resulting solution to thus form precipitates. The precipitates were decanted and then filtered under suction. The resulting filter cake was dried at 120° C. for 5 hours and further calcined at 700° C. for 4 hours. The calcined filter cake was pulverized into fine particles of 10 to 32 mesh and was used as a catalyst.

8 cc of the catalyst was packed in a reactor of stainless steel (SUS 316) having an inner diameter of 17 mm. A mixed gas comprising propane/oxygen/ammonia having a molar ratio of 10/6/3 was supplied at a space velocity (SV) of 1000 $hr^{-1}$ while the temperature of the reactor was maintained at 460° C. After 15 hours, the reaction gas was analyzed and it was found that the conversion of propane was 20%, that of oxygen was 55% and the selectivity of propylene was 67%.

EXAMPLE 6

150.7 g of stannic oxide (available from Kanto Chemical Co., Ltd.) and 77 g of 85% phosphoric acid (available from Junsei Chemical Co., Ltd.) were mixed and then evaporated to dryness. The product was pulverized into fine particles of 10 to 32 mesh and calcined at 700° C. for 4 hours to give a catalyst.

8 cc of the catalyst was packed in a reactor of stainless steel (SUS 316) having an inner diameter of 17 mm. A mixed gas comprising propane/oxygen/ammonia having a molar ratio of 10/6/3 was supplied to the reactor at a space velocity (SV) of 1000 $hr^{-1}$ while the temperature of the reactor was maintained at 460° C. After 15 hours, the reaction gas was analyzed and it was found that the conversion of propane was 12%, that of oxygen was 30% and the selectivity of propylene was 72%.

EXAMPLE 7

The same procedures used in Example 6 were repeated except that the starting gas was diluted with argon so that the molar ratio, argon/propane/oxygen/ammonia, was 20/10/6/3. As a result, it was found that the conversion of propane was 36%, that of oxygen was 98% and the selectivity of propylene was 63%.

EXAMPLE 8

The same procedures used in Example 7 were repeated except that isobutane was substituted for propane, that the starting gas was diluted with argon so that the molar ratio, argon/isobutane/oxygen/ammonia, was 20/10/6/3 and that the reaction was performed at 400° C. As a result, it was found that the conversion of isobutane was 20% and the selectivity of isobutene was 62%.

EXAMPLE 9

Precipitates were prepared in the same manner used in Example 5 and dried. To the resulting powder, there was added a nitrate, chloride or oxide of an element listed in the following Table 1 in an amount of 5 atm % with respect to tin, water was added and kneaded sufficiently, calcinated at 250° C. for 5 hours, then calcined at 700° C. for 4 hours and pulverized into fine particles of 10 to 32 mesh to give a catalyst. Thereafter, 8 cc of the catalyst was packed in a reactor of stainless steel (SUS 316) having an inner diameter of 17 mm. Subsequently, the same procedures used in Example 5 were repeated except that the starting gas was diluted with argon so that the molar ratio, argon/propane/oxygen/ammonia, was 40/10/6/3 and that the reaction was performed at 460° C. Thus, the results listed in the following Table 1 are obtained.

TABLE 1

| Element Added | Conversion of Propane (%) | Propylene Selectivity (%) |
| --- | --- | --- |
| Cs | 25 | 61 |
| Mg | 23 | 63 |
| La | 28 | 64 |
| Ti | 32 | 63 |
| Zr | 38 | 68 |
| Nb | 30 | 65 |
| Al | 35 | 64 |
| As | 38 | 64 |
| Sb | 40 | 68 |
| Te | 38 | 67 |

EXAMPLE 10

The same procedures used in Example 1 were repeated to form precipitates and dried to give dry powder. The dry powder was mixed with 150.7 g of stannic oxide (available from Kanto Chemical Co., Ltd.) and 77 g of 85% phosphoric acid (available from Junsei Chemical Co., Ltd.), the resulting mixture was evaporated to dryness, pulverized into fine particles of 10 to 32 mesh and then calcined at 700° C. for 4 hours to give a catalyst. The same reaction as in Example 1 was performed using the resulting catalyst and as a result it was found that the conversion of propane was 10%, that of oxygen was 27% and the selectivity of propylene was 68%.

COMPARATIVE EXAMPLE 1

The same procedures used in Example 5 were repeated except that ammonia was not used. As a result, it was found that the conversion of propane was 14% and the selectivity of propylene was only 36%.

EXAMPLE 11

354.9 g of indium nitrate (available from Mitsuwa Chemical and Pharmaceutical Co., Ltd.) was added to and dissolved in 3,000 ml of water heated to 40° C. and then a solution of 203.1 g of triammonium phosphate (available from Kanto Chemical Co., Ltd.) in 1,000 ml of water was added to the resulting solution to thus form precipitates. The precipitates were decanted and then filtered under suction 344 g of vanadyl phosphate was added to and kneaded with the resulting filter cake, the resulting mixture was dried at 120° C. for 5 hours and further calcined at 700° C. for 4 hours. The calcined mixture was pulverized into fine particles of 10 to 32 mesh and was used as a catalyst.

8 cc of the catalyst was packed in a reactor of stainless steel (SUS 316) having an inner diameter of 17 mm. A mixed gas comprising propane/oxygen/ammonia having a molar ratio of 10/6/3 was supplied at a space velocity (SV) of 1000 hr$^{-1}$ while the temperature of the reactor was maintained at 370° C. After 15 hours, the reaction gas was analyzed and it was found that the conversion of propane was 12%, the selectivity of propylene was 35% and that of acrylonitrile was 32%.

EXAMPLE 12

The same procedures used in Example 11 were repeated except that the reaction was carried out at 400° C. and after 12 hours, the reaction gas was analyzed. As a result, it was found that the conversion of propane was 18%, the selectivity of propylene was 25% and that of acrylonitrile was 40%.

EXAMPLE 13

The same procedures used in Example 11 were repeated except that isobutane was substituted for propane and that the reaction was carried out at 370° C. As a result, it was found that the conversion of isobutane was 8%, the selectivity of isobutene was 26% and that of methacrylonitrile was 21%.

EXAMPLE 14

The same procedures used in Example 11 were repeated except that 250 g of ammonium molybdate was substituted for 344 g of vanadyl phosphate used in Example 11 and that the reaction was carried out at 390° C. As a result, it was found that the conversion of propane was 16%, the selectivity of propylene was 32% and that of acrylonitrile was 33%.

EXAMPLE 15

The same procedures used in Example 11 were repeated except that 80 g of ammonium tungstate was substituted for 344 g of vanadyl phosphate used in Example 11 and that the reaction was carried out at 415° C. As a result, it was found that the conversion of propane was 9%, the selectivity of propylene was 45% and that of acrylonitrile was 14%.

EXAMPLE 16

225.6 g of tin chloride (available from Kanto Chemical Co., Ltd.) was added to and dissolved in 3,000 ml of a 2N HCl solution heated to 40° C. and then a solution of 380.1 g of trisodium phosphate (available from Kanto Chemical Co., Ltd.) in 1,000 ml of water was added to the resulting solution to thus form precipitates. The precipitates were decanted and then filtered under suction. 344 g of vanadyl phosphate was added to and kneaded with the resulting filter cake, the resulting mixture was dried at 120° C. for 5 hours and further calcined at 700° C. for 4 hours. The calcined mixture was pulverized into fine particles of 10 to 32 mesh and the resulting powdery product was used as a catalyst.

8 cc of the catalyst was packed in a reactor of stainless steel (SUS 316) having an inner diameter of 17 mm. A mixed gas comprising propane/oxygen/ammonia having a molar ratio of 10/6/3 was supplied at a space velocity (SV) of 1000 hr$^{-1}$ while the temperature of the reactor was maintained at 350° C. After 15 hours, the reaction gas was analyzed and it was found that the conversion of propane was 14%, the selectivity of propylene was 28% and that of acrylonitrile was 35%.

EXAMPLE 17

The same procedures used in Example 16 were repeated except that the reaction was carried out at 300° C. As a result, it was found that the conversion of propane was 8%, the selectivity of propylene was 42% and that of acrylonitrile was 28%.

What is claimed is:

1. A method for preparing an $\alpha, \beta$-unsaturated nitrile and a monoolefin wherein a mixed gas comprising paraffin having at least 3 carbon atoms, oxygen and ammonia is brought into contact with a catalyst consisting of phosphorus oxide, at least one of indium oxide and tin oxide and at least one of vanadium oxide, tungsten oxide and molybdenum oxide.

2. The method of claim 1, wherein said paraffin is propane or butane.

3. The method of claim 1, wherein said mixed gas has a molar ratio of paraffin/oxygen/ammonia of 1:0.1–1.0:0.05–0.5.

4. The method of claim 1, wherein the contact between the mixed gas and the catalyst is performed at a temperature of from 200° to 500° C.

5. The method of claim 1, wherein said monoolefin is a $C_3$ or $C_4$ monoolefin.

6. The method of claim 1, wherein said catalyst has a P/Sn or P/In or P(Sn+In) atomic ratio of from 0.05 to 4.

7. The method of claim 1, wherein the contact between the mixed gas and the catalyst is performed at a pressure of from 1 to 3 bar.

8. The method of claim 1, wherein said $\alpha, \beta$-unsaturated nitrile is acrylonitrile or methacrylonitrile.

9. The method of claim 1 wherein said catalyst consists of phosphorus oxide, indium oxide and vanadium oxide.

10. The method of claim 1, wherein said catalyst consists of phosphorus oxide, indium oxide and molybdenum oxide.

11. The method of claim 1, wherein said catalyst consists of phosphorus oxide, indium oxide and tungsten oxide.

12. The method of claim 1, wherein said catalyst consists of phosphorus oxide, tin oxide and vanadium oxide.

* * * * *